US010130627B2

(12) United States Patent
Dungan et al.

(10) Patent No.: US 10,130,627 B2
(45) Date of Patent: Nov. 20, 2018

(54) PHENYLEPHRINE FORMULATIONS WITH IMPROVED STABILITY

(71) Applicant: NOVARTIS CONSUMER HEALTH S.A, Prangins (CH)

(72) Inventors: Timothy Dungan, Lincoln, NE (US); Brian Warrington, Lincoln, NE (US)

(73) Assignee: GlaxoSmithKine Consumer Healthcare S.A., Prangins (CH)

( * ) Notice: Subject to any disclaimer, the term of this patent is extended or adjusted under 35 U.S.C. 154(b) by 65 days.

(21) Appl. No.: 14/729,371

(22) Filed: Jun. 3, 2015

(65) Prior Publication Data

US 2015/0265713 A1    Sep. 24, 2015

Related U.S. Application Data

(63) Continuation-in-part of application No. 13/131,370, filed as application No. PCT/US2009/067618 on Dec. 11, 2009, now abandoned.

(60) Provisional application No. 61/139,391, filed on Dec. 19, 2008.

(51) Int. Cl.
| | |
|---|---|
| *A61K 31/167* | (2006.01) |
| *A61K 31/485* | (2006.01) |
| *A61K 31/137* | (2006.01) |
| *A61K 9/16* | (2006.01) |
| *A61K 9/20* | (2006.01) |
| *A61K 31/375* | (2006.01) |
| *A61K 31/4402* | (2006.01) |

(52) U.S. Cl.
CPC .......... *A61K 31/485* (2013.01); *A61K 9/1652* (2013.01); *A61K 9/205* (2013.01); *A61K 31/137* (2013.01); *A61K 31/167* (2013.01); *A61K 31/375* (2013.01); *A61K 31/4402* (2013.01)

(58) Field of Classification Search
CPC .................................................... A61K 31/167
See application file for complete search history.

(56) References Cited

U.S. PATENT DOCUMENTS

| | | | |
|---|---|---|---|
| 7,355,042 B2 | 4/2008 | Edgar et al. | 540/542 |
| 2002/0022057 A1* | 2/2002 | Battey | A61K 9/0056 424/490 |
| 2006/0127473 A1* | 6/2006 | Nichols | A61K 9/2054 424/464 |
| 2008/0181932 A1 | 7/2008 | Bortz et al. | 424/439 |
| 2009/0047343 A1 | 2/2009 | Huang et al. | |
| 2009/0215811 A1 | 8/2009 | Atkinson | |
| 2009/0220594 A1 | 9/2009 | Field | |

OTHER PUBLICATIONS

The Harvard Health Letter, Active ingredients in selected cold medicines, Jan. 2008, available at http://www.health.harvard.edu/newsletter_article/active_ingredients_in_selected_cold_medicines.*
Tebrock et al., Usefulness of bioflavonoids and ascorbic acid in treatment of common cold, JAMA, vol. 162, No. 13, pp. 1227-1233, Nov. 24, 1986.*
Kleinebudde, Roll compaction/ dry granulation: pharmaceutical applications, European Journal of Pharmaceutics and Biopharmaceutics 58 (2004) 317-326.*
U.S. Appl. No. 14/725,098, filed May 2015, Dungan.*
Lacy et al., Drug Information Handbook, 7th Edition, 1999-2000.

* cited by examiner

*Primary Examiner* — Svetlana M Ivanova
(74) *Attorney, Agent, or Firm* — Joshua C. Sanders

(57) ABSTRACT

A pharmaceutical composition includes a pharmaceutical polysaccharide and phenylephrine hydrochloride. The ratio of said polysaccharide to phenylephrine hydrochloride is sufficient to dilute the composition such that phenylephrine hydrochloride is stable at high temperature and humidity.

14 Claims, No Drawings

PHENYLEPHRINE FORMULATIONS WITH IMPROVED STABILITY

CROSS-REFERENCE TO RELATED APPLICATIONS

The present application claims priority to and is a continuation-in-part of U.S. application Ser. No. 13/131370 filed on May 26, 2011, which is the national stage filing of PCT/US09/67618 filed on Dec. 11, 2009, which claims priority to U.S. Provisional Application Ser. No. 61/139,391 filed on Dec. 19, 2008, which are incorporated herein by reference for all purposes.

BACKGROUND OF THE INVENTION

This application relates to phenylephrine hydrochloride-containing formulations having improved stability and thus increased shelf life.

Phenylephrine hydrochloride (PHL) is a decongestant frequently used in over-the-counter (OTC) cough and cold preparations. PHL is a reactive molecule that undergoes reactions with numerous excipients commonly used in OTC preparations to form other species, with a corresponding decrease in the amount of active PHL in the product. This can lead to a need to set shorter expiration times than may be considered optimum for OTC products.

While many of the reactions of PHL occur at room temperature and conventional indoor humidity conditions, the reaction rates are higher at elevated temperatures and elevated humidity. OTC preparations intended for sale in Climatic Zones with high ambient temperature and humidity (Climatic Zones 3 (30° C./35% relative air humidity) and 4 (30° C./70% or greater relative air humidity) therefore may have significantly shorter shelf life which may make the product unmarketable in these regions.

SUMMARY OF THE INVENTION

The present invention provides a PHL formulation, preferably in unit dose form, that provides stability sufficient for a shelf life of 24 months, even under high temperature and high humidity conditions. In accordance with the invention, the formulation comprises phenylephrine hydrochloride and a polysaccharide in a weight ratio of at least 1:20, preferably at least 1:30, and most preferably at least 1:40. The polysaccharide used may be maltodextrin. The formulation may also comprise additional active pharmaceutical ingredients (APIs) for cough, cold, and/or congestion, such as diphenhydramine hydrochloride, acetaminophen, dextromethorphan hydrobromide, pheniramine maleate, and chlorpheniramine maleate in conventional amounts relative to the amount of phenylephrine hydrochloride, as well as additional excipients.

The invention also provides a method of making a pharmaceutical granulation, performed by combining a pharmaceutical polysaccharide with PHL and processing to form a pharmaceutical granulation. The amount of the polysaccharide must be sufficient to dilute the PHL such that PHL is stable at high temperature and humidity. The weight ratio of phenylephrine hydrochloride to the polysaccharide should be at least 1:20, preferably at least 1:30, and most preferably at least 1:40. The polysaccharide used may be maltodextrin. In addition, the processing may be performed by using a roller compactor-mill-sieve equipment train.

DESCRIPTION OF DRAWINGS

There are no drawings.

DETAILED DESCRIPTION OF THE INVENTION

The present invention provides a way to improve stability of phenylephrine hydrochloride (PHL), for example, in over-the-counter cough and cold preparations. As used in this specification, "stable" means that a composition containing PHL has an assayed value of greater than 95.0% of the labeled content after 24 months in Climatic Zone 3 (30° C./35% relative air humidity).

To practice the invention, maltodextrin is used in sufficient quantities to dilute PHL at a weight ratio at least of 1:20 and preferably at least 1:30, and most preferably at least 1:40.

Conventional manufacturing procedures require the preparation of a composition, which is a powdered or granulated admixture of the active ingredients of a tablet, a binder material and excipients. Without intending to be bound by any particular mechanism, it is believed that the maltodextrin serves as a dry binder and diluent in the formulation, and increases the distance between PHL and reactive excipients or actives. Other pharmaceutical grade polysaccharides may provide similar results. This includes: cellulose, starch, hyaluronan, chitin and chitosan.

To arrive at the composition of the present invention, the Inventor tested several preparations. The preparations were subjected to high heat and humidity (40° C./75% relative humidity) and stability data was collected over six months. This accelerated stability data is an indicator of 24-month real data, based on the Arrhenius equation, which correlates temperature and reaction rate. Preparations utilizing the invention showed PHL stability over six months sufficient to indicate stability for Climate Zones 3 and 4 with a shelf life of 24 months or greater.

In addition, a method of making a pharmaceutical composition is disclosed. To make the pharmaceutical composition, a pharmaceutical polysaccharide and PHL are combined, and then mixed to form a pharmaceutical composition. The amount of polysaccharide must be sufficient to dilute the phenylephrine so that it is stable at high temperature and humidity. The composition should be mixed sufficiently so that it is "macroscopically homogeneous," meaning that the active ingredients are substantially evenly dispersed such that a random sample of the composition will contain a proportional amount of each component. The pharmaceutical composition may later be processed into unit dose form.

EXAMPLES

Example 1

A preparation was made containing 650 mg acetaminophen, 25 mg diphenhydramine hydrochloride, 10 mg phenylephrine hydrochloride, 312 mg maltodextrin, and other excipients per dose. These other excipients included 0.7 mg pharmaceutical-quality dyes, 11.9 mg silicon dioxide, 938 mg natural flavors, 450 mg citric acid, 81 mg sodium citrate, 35 mg calcium phosphate tribasic, and 46 mg high intensity sweeteners. 7500 mg sucrose was added during packaging. The mixture was passed through a roller compactor-mill-sieve equipment train multiple times to achieve particles with an optimal size for further processing. This mixture was further processed into unit dose form.

When this preparation was subjected to high heat and humidity (40° C./75% relative humidity), total phenylephrine hydrochloride degradation (calculated as the % reacted of the labeled content of phenylephrine hydrochloride) was 0.43 at 3 months and 0.81 at 6 months, from an initial degradation of 0.10. In addition, after 24 months storage at 25° C./60% relative humidity, total phenylephrine hydrochloride degradation was calculated to be 0.31.

These values correlate to an assay value of not less than 95% of the labeled amount of PHL at the minimum desired shelf life of 24 months in Climate Zones 3 and 4.

Example 2

A preparation was made containing 650 mg acetaminophen, 20 mg dextromethorphan hydrobromide, 10 mg phenylephrine hydrochloride, 456 mg maltodextrin, and other excipients per dose. These other excipients included 3.7 mg pharmaceutical-quality dyes, 11.9 mg silicon dioxide, 638 mg natural flavors, 705 mg citric acid, 81 mg sodium citrate, 35 mg calcium phosphate tribasic, and 50 mg high intensity sweeteners. 7500 mg sucrose was added during packaging. The mixture was passed through a roller compactor-mill-sieve equipment train multiple times to achieve particles with an optimal size for further processing. This mixture was further processed into unit dose form.

When this preparation was subjected to high heat and humidity (40° C./75% relative humidity), total phenylephrine hydrochloride degradation (calculated as the % reacted of the labeled content of phenylephrine hydrochloride) was 0.44 at 3 months and 0.61 at 6 months, from an initial degradation of 0.21. In addition, after 24 months storage at 25° C./60% relative humidity, total phenylephrine hydrochloride degradation was calculated to be 0.41.

These values correlate to an assay value of not less than 95% of the labeled amount of PHL at the minimum desired shelf life of 24 months in Climate Zones 3 and 4.

Example 3

A preparation is made containing 650 mg acetaminophen, 20 mg pheniramine maleate, 10 mg phenylephrine hydrochloride, 400-600 mg maltodextrin, 50 mg ascorbic acid and other excipients per dose. These other excipients include 0.6-1.58 mg pharmaceutical-quality dyes, 18 mg silicon dioxide, 210-473 mg natural flavors, 650-1000 mg citric acid, 115-180 mg sodium citrate, 35 mg calcium phosphate tribasic, 8-50 mg high intensity sweeteners. An additional 14 g sucrose is added during packaging. The pheniramine maleate and phenylephrine hydrochloride are compacted separately. The mixture is passed through a roller compactor-mill-sieve equipment train multiple times to achieve particles with an optimal size for further processing. This mixture is further processed into unit dose form.

The invention claimed is:
1. A composition comprising:
  phenylephrine hydrochloride and a dry binder consisting essentially of maltodextrin;
  wherein the weight ratio of the phenylephrine hydrochloride to the maltodextrin is at least 1:20 and is sufficient to dilute the composition such that the phenylephrine hydrochloride is stable at a temperature of 30° C. and above and relative humidity of 35% and above.

2. The composition of claim 1, wherein the weight ratio of the phenylephrine hydrochloride to the maltodextrin is at least 1:30.

3. The composition of claim 1, wherein the weight ratio of the phenylephrine hydrochloride to the maltodextrin is at least 1:40.

4. The composition of claim 1 comprising 650 mg of acetaminophen, 25 mg of diphenhydramine hydrochloride, 10 mg of phenylephrine hydrochloride and 312 mg of maltodextrin per dose.

5. The composition of claim 1 comprising 650 mg of acetaminophen, 20 mg of dextromethorphan hydrobromide, 10 mg of phenylephrine hydrochloride and 456 mg of maltodextrin per dose.

6. The composition of claim 1 comprising 650 mg of acetaminophen, 20 mg of pheniramine maleate, 10 mg of phenylephrine hydrochloride, 400-600 mg of maltodextrin and 50 mg ascorbic acid.

7. The composition of claim 1 wherein when the composition is exposed to a temperature of 30° C. and 70% relative humidity for 24 months, at least 95% of an original amount of the phenylephrine hydrochloride is still present in the composition.

8. The composition of claim 1 wherein the composition is processed by roller compactor-mill-sieve equipment.

9. A method of making a composition according to claim 1 comprising combining maltodextrin and phenylephrine hydrochloride; and mixing to form a pharmaceutical composition;
  wherein the amount of the maltodextrin is sufficient to dilute the phenylephrine hydrochloride such that the phenylephrine hydrochloride is stable at a temperature of 30° C. and above and relative humidity of 35% and above.

10. The method of claim 9, wherein the weight ratio of the phenylephrine hydrochloride to the maltodextrin is at least 1:30.

11. The method of claim 9, wherein the weight ratio of the phenylephrine hydrochloride to the maltodextrin is at least 1:40.

12. The method of claim 9 wherein the composition comprises 650 mg of acetaminophen, 25 mg of diphenhydramine hydrochloride, 10 mg of phenylephrine hydrochloride and 312 mg of maltodextrin per dose.

13. The method of claim 9 wherein the composition comprises 650 mg of acetaminophen, 20 mg of dextromethorphan hydrobromide, 10 mg of phenylephrine hydrochloride and 456 mg of maltodextrin per dose.

14. The method of claim 9 wherein the composition comprises 650 mg of acetaminophen, 20 mg of pheniramine maleate, 10 mg of phenylephrine hydrochloride, 400-600 mg of maltodextrin and 50 mg ascorbic acid.

* * * * *